United States Patent [19]

Bukowski

[11] 4,195,625
[45] Apr. 1, 1980

[54] GUM CLEANING IMPLEMENT
[75] Inventor: Michelene F. Bukowski, Los Angeles, Calif.
[73] Assignee: Mark F. Bukowski
[21] Appl. No.: 914,537
[22] Filed: Jun. 12, 1978
[51] Int. Cl.² ............................................. A61L 7/00
[52] U.S. Cl. .................................. 128/62 A; 433/147
[58] Field of Search ........................... 32/58, 40 R, 34; 128/62 A; 15/167 R, 210 R

[56] References Cited
U.S. PATENT DOCUMENTS

| 1,637,738 | 8/1927  | Cough   | 15/167 R |
| 1,660,095 | 2/1928  | Schiele | 128/62 A |
| 1,796,367 | 3/1931  | Grove   | 32/58    |
| 1,804,240 | 5/1931  | Welsh   | 15/210 R |
| 1,996,205 | 4/1935  | Jackson | 128/62 A |
| 2,134,934 | 11/1938 | Wilhoit | 128/62 A |
| 2,233,831 | 3/1941  | Burke   | 15/167 R |
| 2,719,315 | 10/1955 | Sheehan | 15/167 R |
| 2,872,929 | 2/1959  | Rice    | 128/62 A |
| 3,321,796 | 5/1967  | Lelicoff| 15/167 R |
| 3,552,022 | 1/1971  | Axelsson| 32/58    |

Primary Examiner—Louis G. Mancene
Assistant Examiner—John J. Wilson
Attorney, Agent, or Firm—Bruce L. Birchard

[57] ABSTRACT

A hand-held implement with a specially contoured, flexible tip covered by a physically strong but absorbent fabric securely but removable held in place over such tip permits cleansing of the gums of denture wearers on a safe and sanitary basis.

3 Claims, 5 Drawing Figures

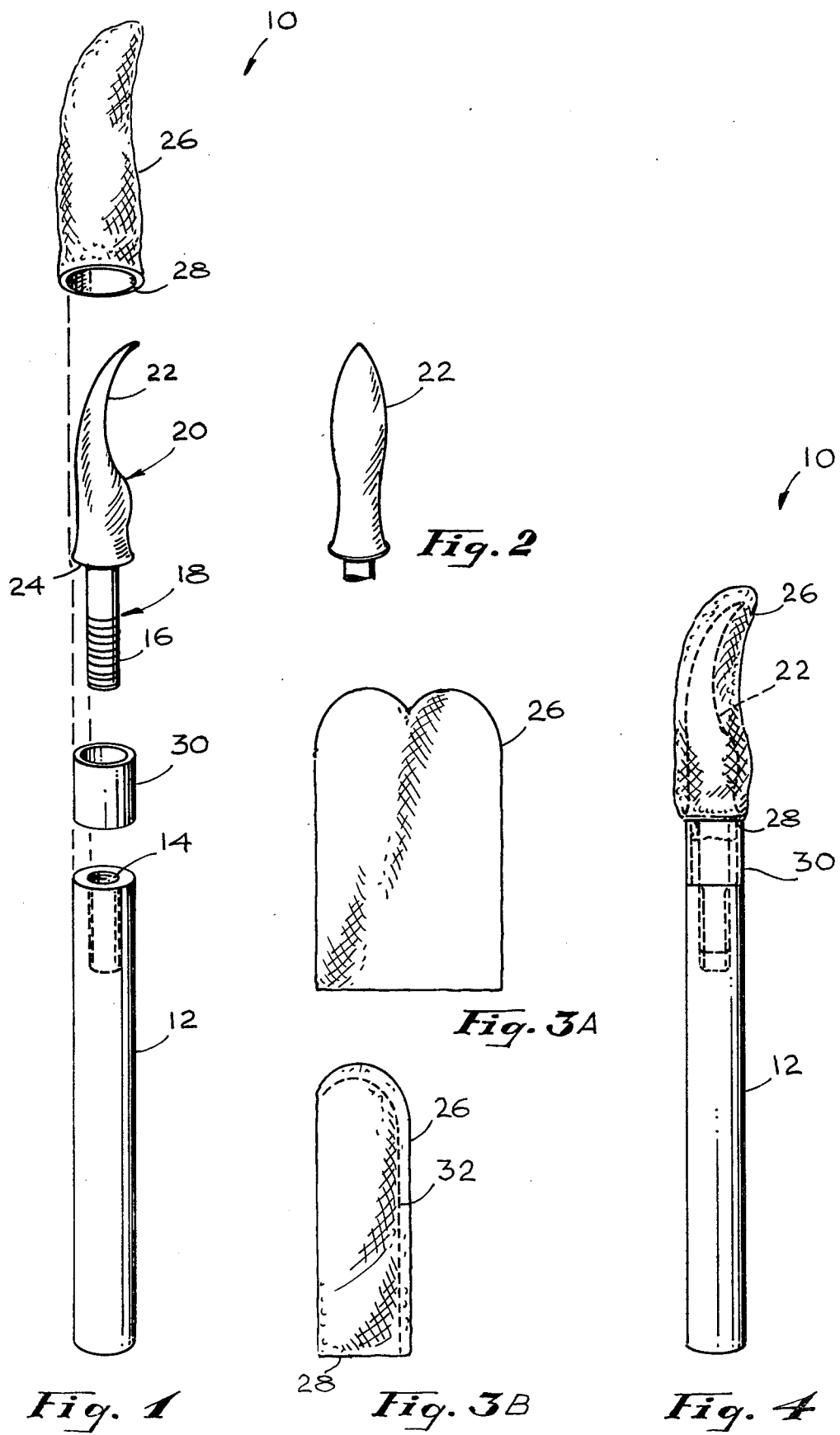
U.S. Patent  Apr. 1, 1980  4,195,625

GUM CLEANING IMPLEMENT

BACKGROUND OF THE INVENTION

1. Field of the Invention

This invention relates to oral hygiene apparatus and, more specifically, to apparatus for cleansing gums and other portions of the mouth.

2. Description of the Prior Art

A search of the Patent Office records has revealed the following patents which are deemed by this inventor to be pertinent but not, separately or in combination, anticipatory of this invention:

| U.S. Pat. No. | Inventor |
| --- | --- |
| 1,470,710 | Davis |
| 2,077,758 | Johnson, et al |
| 2,233,831 | Burke |
| 2,419,896 | Hobelmann |
| 2,474,684 | McCaughley |
| 2,719,315 | Sheehan |
| 2,585,061 | Wester, Jr. |
| 2,872,929 | Rice |
| 3,321,796 | Lelicoff |
| 3,139,094 | Efeian |

SUMMARY OF THE INVENTION

My invention is particularly useful to those persons wearing dentures. However, it is also useful to other persons following extractions or oral surgery and during periods of oral infections when the mouth and gums are in a sensitive state.

A denture wearer has a special problem. There are many ways to clean dentures but, until my invention, there has been no gentle, effective way to cleanse the gums, tongue and mouth.

Toothbrushes are painful and harmful to sensitive gum tissue. Mouthwashes are ineffective in removing residual materials, such as food, denture adhesives and other such materials from the crevices and scar tissue in the gums.

The specially tapered curve of the flexible tip in the apparatus according to my invention allows the tip to slip into every part of the mouth. The soft, textured cover for the tip cleans thoroughly but does not deteriorate in use, as would a cotton swab.

The tip-cover may be washed and re-used. While the cover may be easily removed, when such removal is desired, accidental removal of the cover from the tip during use of the implement is not possible because of the securing action of a retaining ring which overlaps the cover at its open end and presses the end of the cover against a cooperating shoulder. This safety feature prevents possible choking or any other untoward incident which might occur if the cover became loose in the mouth of the user of the implement. In these days of public awareness of product safety and assertion of product liability claims this safety feature gains added significance.

Assembly and cover replacement have been made simple to ease potential problems for users of advanced age or of limited sight or dexterity.

BRIEF DESCRIPTION OF THE DRAWINGS

The features of the present invention which are believed to be novel are set forth with particularity in the appended claims. The present invention, both as to its organization and manner of operation, together with further objects and advantages thereof, may be best understood by reference to the following description taken in conjunction with the accompanying drawings, in which:

FIG. 1 is an exploded view of a gum cleaning implement according to my invention;

FIG. 2 is a back elevational view of a portion of the implement of FIG. 1;

FIG. 3A is an elevational view of a pattern for the cover portion of the implement of FIG. 1;

FIG. 3B is an elevational view of the cover formed from the pattern of FIG. 3A; and FIG. 4 is an elevational view of the assembled implement made according to my invention.

DETAILED DESCRIPTION OF THE PREFERRED EMBODIMENT

In FIG. 1, implement 10 includes handle 12 which may be cylindrical, as shown, or may have any other shape which permits easy gripping and manipulation of the implement. Handle 12, at one end, has threaded recess 14 for receiving the male-threaded portion 16 on stem 18 of tip portion 20. Means other than threads, for example a bayonet type of connector, may be used to connect handle 12 to tip portion 20. Tip portion 20 includes stem 18 and tip 22, which may be formed integrally from a thermosetting plastic. Tip 22 has a concavo-convex configuration with a taper in both its width and thickness dimensions, as can be seen from FIGS. 1 and 2. The bi-dimensional taper permits insertion in remote regions of the mouth for effective and thorough cleaning of the gums. The material of which tip 22 is made must be such as to provide flexibility and superficial softness but, also, a degree of strength and rigidity so that stubborn residuum on the gums may be removed, safely. Many plastic materials exhibit these joint characteristics, e.g. a polyethylene.

Because of the reduced diameter of stem 18 with respect to tip 22 a shoulder 24 is formed. Threaded portion 16 of stem 18 is spaced from shoulder 24 for about one-half inch, for reasons which are described immediately hereinafter.

Cover 26 is a sleeve formed, as described in connection with FIGS. 3 and 3A, from a strong, soft and absorbent material, such as terry cloth. The length of cover 26 exceeds that length of tip 22 by a small amount, say one-fourth inch, so that the open end 28 of cover 26 overlaps shoulder 24 and the unthreaded portion of stem 18.

Securing ring 30 has a length which approximates, but slightly exceeds, the length of the unthreaded portion of stem 18. The internal diameter of ring 30 exceeds the external diameter of stem 18 sufficiently to permit ring 30 to slip over the lower end 28 of cover 26. The outer diameter of sleeve 30 approximates the outer diameter of shoulder 24. Thus, ring 30 has a wall thickness approximating one-sixteenth inch. The surface material of ring 30 should be rust-proof and tarnish-proof, as for example, may be obtained by chromium plating a steel base material.

Cover 26 may be formed from stretch terry cloth, as shown in FIGS. 3 and 3A. The terry cloth may be made of natural or synthetic fibers, or a mixture thereof.

The fabric should be woven with its absorbent loops on one side only. The weft or warp threads should have a minimum stretch of one-fourth inch per inch of material. The fabric must be color fast and not subject to rapid deterioration when subjected to sterilization procedures.

In FIG. 3A the unsewn fabric in the desired pattern for cover 26 is shown. The fabric is cut so that its long dimension corresponds to the direction of the warp of the fibers used in making the cover. The width of the cover corresponds to the weft of the fibers to give stretch to the cover. The folded fabric is stitched about one-eighth inch from its edge, as shown at 32 in FIG. 3B. The bottom edge 28 is left open.

As is shown in FIG. 4, when implement 10 is assembled, cover 26 is slipped over tip 22 and its bottom edge 28 extends over shoulder 24 and around the upper region of the unthreaded portion of stem 18. Securing ring 30 is slipped over the bottom edge 28 of cover 26, threaded portion 16 of stem 18 is inserted in the threaded recess 15 in handle 12 and the handle 12 and tip portion 20 are turned relative to each other until ring 30 is urged snugly towards shoulder 24 by handle 12, capturing the bottom edge 28 of cover 26 between ring 30 and shoulder 24, thus assuring that cover 26 will not become loose accidentally in the mouth of the user of implement 10. At the same time, by reversing the process, cover 26 may be removed, intentionally, for cleaning, sterilization or replacement.

While a particular embodiment of my invention has been shown and described it will be apparent to those skilled in the art that variations on this embodiment may be made without departing from the scope and spirit of my invention. It is the purpose of the appended claims to cover all such variations.

I claim:

1. An oral implement, including:
    a tip portion, said tip portion including a tip and a stem, and stem hving a threaded portion remote from said tip and an unthreaded portion between said threaded portion and said tip, said stem having a diameter less than the diameter of said tip at the juncture between said stem and said tip, whereby a shoulder is formed;
    a cover configured to envelope said tip and having a lower, open end extending beyond said shoulder when said cover is in position on said tip;
    a handle having a common direction with said tip portion and having a threaded recess in one end thereof dimensioned to receive said threaded portion of said stem; and,
    a ring, having an inside diameter exceeding the diameter of said stem and a length corresponding to the length of said unthreaded portion of said stem;
    said ring surrounding said stem, receiving said cover in the space between said inner diameter of said ring and said stem and forcefully securing said lower, open end of said cover against said shoulder when said threaded portion of said stem is in cooperative engagement with said threaded recess in said handle;
    said tip being tapered in both its width and and thickness dimensions and having a concavo-convex configuration.

2. Apparatus according to claim 1 in which said cover is of an absorbent fabric.

3. Apparatus according to claim 2 in which said tip is of a pliable plastic.

* * * * *